(12) United States Patent
Kim et al.

(10) Patent No.: US 11,246,939 B2
(45) Date of Patent: Feb. 15, 2022

(54) IMMUNOREGULATORY PROTEIN-SIRNA COMPLEX HAVING ANTICANCER ACTIVITY

(71) Applicant: KOREA INSTITUTE OF SCIENCE AND TECHNOLOGY, Seoul (KR)

(72) Inventors: Sun Hwa Kim, Seoul (KR); Ick Chan Kwon, Seoul (KR); In-San Kim, Seoul (KR); Kwangmeyung Kim, Seoul (KR); Yoosoo Yang, Seoul (KR); Young-Ji Ko, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 16/573,351

(22) Filed: Sep. 17, 2019

(65) Prior Publication Data
US 2021/0015931 A1     Jan. 21, 2021

(30) Foreign Application Priority Data
Jul. 16, 2019 (KR) .................. 10-2019-0085912

(51) Int. Cl.
| | | |
|---|---|---|
| *A61K 47/55* | (2017.01) | |
| *A61K 47/54* | (2017.01) | |
| *A61K 31/713* | (2006.01) | |
| *C12N 15/113* | (2010.01) | |
| *C07K 14/705* | (2006.01) | |
| *A61P 35/00* | (2006.01) | |
| *A61K 38/00* | (2006.01) | |

(52) U.S. Cl.
CPC ............ *A61K 47/55* (2017.08); *A61K 31/713* (2013.01); *A61K 47/549* (2017.08); *A61P 35/00* (2018.01); *C07K 14/70596* (2013.01); *C12N 15/1138* (2013.01); *A61K 38/00* (2013.01); *C12N 2310/3513* (2013.01)

(58) Field of Classification Search
None
See application file for complete search history.

(56) References Cited

U.S. PATENT DOCUMENTS

| | | | |
|---|---|---|---|
| 2017/0107270 A1* | 4/2017 | Pons .................... | A61P 3/10 |
| 2021/0015931 A1 | 1/2021 | Kim et al. | |

FOREIGN PATENT DOCUMENTS

| | | |
|---|---|---|
| KR | 2007/0061770 A | 6/2007 |
| KR | 2015/0039259 A | 4/2015 |
| KR | 10-2018-0134424 A | 12/2018 |
| KR | 10-1977532 B1 | 5/2019 |
| WO | WO-2017/053720 A1 | 3/2017 |

OTHER PUBLICATIONS

Hatherley et al. "Polymorphisms in the Human Inhibitor Signal-regulatory Protein alpha Do Not Affect Binding to Its Ligand CD47" J. Biol. Chem. 289:10024-10028. (Year: 2014).*
Wang et al., "Intravenous Delivery of siRNA Targeting CD47 Effectively Inhibits Melanoma Tumor Growth and Lung Metastasis," Molecular Therapy, 21(10): 1919-1929 (2013).

* cited by examiner

*Primary Examiner* — Sudhakar Katakam
*Assistant Examiner* — Zachary J Miknis
(74) *Attorney, Agent, or Firm* — Foley Hoag LLP; Dana Gordon; Mohanad Mossalam

(57) ABSTRACT

A fusion protein-siRNA complex according to the present disclosure binds specifically to cancer cells, is taken up effectively by the cells, and exhibits anticancer activity as it is degraded by lysosomes. The fusion protein-siRNA complex provides maximized anticancer activity so that the cancer cells can be removed by autoimmunity, by inhibiting the immunity of the cancer cells and enhancing phagocytosis by macrophages.

6 Claims, 9 Drawing Sheets
Specification includes a Sequence Listing.

SEQUENCE LISTING

<160> NUMBER OF SEQ ID NOS: 20

<210> SEQ ID NO 1
<211> LENGTH: 130
<212> TYPE: PRT
<213> ORGANISM: Artificial Sequence
<220> FEATURE:
<223> OTHER INFORMATION: Synthetic peptide (fusion protein)

<400> SEQUENCE: 1

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

```
Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Val Asp Gly Gly Phe Leu Gly Gly Gly Gly
        115                 120                 125

Cys Gly
    130

<210> SEQ ID NO 2
<211> LENGTH: 405
<212> TYPE: DNA
<213> ORGANISM: Artificial Sequence
<220> FEATURE:
<223> OTHER INFORMATION: Synthetic nucleotide (the coding sequence of
      the fusion protein (SEQ ID NO: 1))

<400> SEQUENCE: 2
catatggaag aggagctgca gatcatccag cctgacaagt ccgtgctggt cgctgctggt      60
gaaactgcca ctctgcgttg tacgattacc agcctgttcc cggtgggtcc aatccagtgg     120
ttccgtggtg ctggtccggg tcgtgttctg atctacaacc agcgtcaagg tccgttcccg     180
cgtgtaacta ccgttagcga taccacgaag cgtaacaaca tggactttc catccgcatt      240 ggcaatatta ccccggccga cgcgggcacc tactattgca tcaaatttcg caaaggctcc     300
ccggatgatg tagaatttaa atctggcgca ggcaccgaac tgtctgttcg cgcaaaaccg     360
gtcgacggtg gctttctggg tggcggtggc tgcggttgaa agctt                     405

<210> SEQ ID NO 3
<211> LENGTH: 118
<212> TYPE: PRT
<213> ORGANISM: Artificial Sequence
<220> FEATURE:
<223> OTHER INFORMATION: Synthetic peptide (variant S1PR alpha protein)

<400> SEQUENCE: 3

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro
        115

<210> SEQ ID NO 4
<211> LENGTH: 354
<212> TYPE: DNA
<213> ORGANISM: Artificial Sequence
<220> FEATURE:
<223> OTHER INFORMATION: Synthetic nucleotide (variant S1PR alpha
``` protein coding sequence)

<400> SEQUENCE: 4

```
gaagaggagc tgcagatcat ccagcctgac aagtccgtgc tggtcgctgc tggtgaaact    60
gccactctgc gttgtacgat taccagcctg ttcccggtgg gtccaatcca gtggttccgt   120
ggtgctggtc cgggtcgtgt tctgatctac aaccagcgtc aaggtccgtt cccgcgtgta   180
actaccgtta gcgataccac gaagcgtaac aacatggact tttccatccg cattggcaat   240
attaccccgg ccgacgcggg cacctactat tgcatcaaat tcgcaaagg ctccccggat    300 gatgtagaat taaatctgg cgcaggcacc gaactgtctg ttcgcgcaaa accg          354
```

<210> SEQ ID NO 5
<211> LENGTH: 118
<212> TYPE: PRT
<213> ORGANISM: Artificial Sequence
<220> FEATURE:
<223> OTHER INFORMATION: Synthetic peptide (wild type SIRP alpha coding sequence)

<400> SEQUENCE: 5

```
Glu Glu Glu Leu Gln Val Ile Gln Pro Asp Lys Ser Val Leu Val Ala
 1               5                  10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro
        115
```

<210> SEQ ID NO 6
<211> LENGTH: 354
<212> TYPE: DNA
<213> ORGANISM: Artificial Sequence
<220> FEATURE:
<223> OTHER INFORMATION: Synthetic nucleotide (wild type SIRP alpha coding sequence)

<400> SEQUENCE: 6

```
gaggaggaat acaggtcat tcaaccagat aaatcggtct tagtagcagc cggagagaca    60
gctacattga tgtacggc gacaagcctt attcccgtgg ggccgatcca atggtttcgc    120
ggggcaggcc ccggaagaga attgatttac aaccagaagg agggtcattt ccctcgcgtg   180
acgacggtca gcgacttaac taagcgtaat aacatggatt tttcaataag aataggcaat   240
ataactccgg ccgacgcagg gacgtactac tgtgttaaat ccggaagggg atctccggat   300
gatgtcgagt tcaaatctgg ggcgggtaca gaattgagcg ttcgggcaaa gccc         354
```

<210> SEQ ID NO 7
<211> LENGTH: 119
<212> TYPE: PRT
<213> ORGANISM: Artificial Sequence
<220> FEATURE:
<223> OTHER INFORMATION: Synthetic peptide (wild type SIRPg protein)

<400> SEQUENCE: 7

Glu Glu Glu Leu Gln Met Ile Gln Pro Glu Lys Leu Leu Val Thr
1               5                  10                  15

Val Gly Lys Thr Ala Thr Leu His Cys Thr Val Thr Ser Leu Leu Pro
            20                  25                  30

Val Gly Pro Val Leu Trp Phe Arg Gly Val Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro Ser
        115

<210> SEQ ID NO 8
<211> LENGTH: 354
<212> TYPE: DNA
<213> ORGANISM: Artificial Sequence
<220> FEATURE:
<223> OTHER INFORMATION: Synthetic nucleotide (wild type SIRPg coding
      sequence)

<400> SEQUENCE: 8
gaggaagaat tgcaaatgat ccagccggaa aaattattac tggttaccgt gggaaaaacg      60
gcgacccttc attgcacagt cacgtccctg ttgccggtag gtccagtttt gtggttccgg    120
ggggttggac cagggcgtga actgatctat aatcaaaagg aaggtcattt ccgcgcgtg     180 accacagtga gcgatttgac taaacggaac aatatggact ctcgatccg catttctagt    240 attacaccgg cggacgttgg cacttattat tgcgtcaagt tccgcaaagg aagtcctgag   300
aacgtagagt tcaagtccgg tcctggcact gagatggctt tgggtgctaa accc          354

<210> SEQ ID NO 9
<211> LENGTH: 118
<212> TYPE: PRT
<213> ORGANISM: Artificial Sequence
<220> FEATURE:
<223> OTHER INFORMATION: Synthetic peptide (SIRPg variant 1 protein)

<400> SEQUENCE: 9

Glu Glu Glu Leu Gln Ile Ile Gln Pro Glu Lys Leu Leu Leu Val Thr
1               5                  10                  15

Val Gly Lys Thr Ala Thr Leu His Cys Thr Ile Thr Ser Leu Phe Pro
            20                  25                  30

Val Gly Pro Val Leu Trp Phe Arg Gly Val Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro
        115

<210> SEQ ID NO 10
<211> LENGTH: 354
<212> TYPE: DNA
<213> ORGANISM: Artificial Sequence
<220> FEATURE:
<223> OTHER INFORMATION: Synthetic nucleotide (SIRPg variant 1 coding
      sequence)

<400> SEQUENCE: 10
gaagaggaat tacaaatcat acaacctgaa aagctgttat tggtcaccgt aggcaaaacc      60
gctactctgc actgcactat tacgtccctt tttcctgttg gtcctgtctt atggtttcgt     120
ggagtcggtc cgggtcgggt tcttatctat aaccagcggc aaggaccatt cccacgggtt     180
accacggttt cggacacaac gaaacgcaat aacatggatt tttccattcg gatttcaagc     240
atcactccgg ccgacgttgg aacttattac tgcataaagt ttagaaaggg atctccggag     300
aacgtagaat taagtctgg tccaggtact gagatggccc ttggagcgaa gccg            354

<210> SEQ ID NO 11
<211> LENGTH: 118
<212> TYPE: PRT
<213> ORGANISM: Artificial Sequence
<220> FEATURE:
<223> OTHER INFORMATION: Synthetic peptide (SIRPg variant 2 protein)

<400> SEQUENCE: 11

Glu Glu Glu Leu Gln Ile Ile Gln Pro Glu Lys Leu Leu Leu Val Thr
1               5                   10                  15

Val Gly Lys Thr Ala Thr Leu His Cys Thr Val Thr Ser Leu Phe Pro
            20                  25                  30

Val Gly Pro Val Leu Trp Phe Arg Gly Val Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro
        115

<210> SEQ ID NO 12
<211> LENGTH: 354
<212> TYPE: DNA
<213> ORGANISM: Artificial Sequence
<220> FEATURE:
<223> OTHER INFORMATION: Synthetic nucleotide (SIRPg variant 2 coding
      sequence)

<400> SEQUENCE: 12
gaagaggaat tacaaatcat acaacctgaa aagctgttat tggtcaccgt aggcaaaacc      60
gctactctgc actgcactgt gacgtccctt tttcctgttg gtcctgtctt atggtttcgt     120

```
ggagtcggtc cgggtcgggt tcttatctat aaccagcggc aaggaccatt cccacgggtt    180
accacggttt cggacacaac gaaacgcaat aacatggatt tttccattcg gatttcaagc    240
atcactccgg ccgacgttgg aacttattac tgcataaagt ttagaaaggg atctccggag    300
aacgtagaat ttaagtctgg tccaggtact gagatggccc ttggagcgaa gccg          354
```

```
<210> SEQ ID NO 13
<211> LENGTH: 10
<212> TYPE: PRT
<213> ORGANISM: Artificial Sequence
<220> FEATURE:
<223> OTHER INFORMATION: Synthetic peptide (linker)

<400> SEQUENCE: 13

Gly Gly Phe Leu Gly Gly Gly Gly Cys Gly
1               5                   10

<210> SEQ ID NO 14
<211> LENGTH: 30
<212> TYPE: DNA
<213> ORGANISM: Artificial Sequence
<220> FEATURE:
<223> OTHER INFORMATION: Synthetic nucleotide (linker)

<400> SEQUENCE: 14
ggtggctttc tgggtggcgg tggctgcggt                                      30

<210> SEQ ID NO 15
<211> LENGTH: 24
<212> TYPE: DNA
<213> ORGANISM: Artificial Sequence
<220> FEATURE:
<223> OTHER INFORMATION: Synthetic nucleotide (SPIR alpha linker F)

<400> SEQUENCE: 15
aaacatatgg aagaggagct gcag                                            24

<210> SEQ ID NO 16
<211> LENGTH: 27
<212> TYPE: DNA
<213> ORGANISM: Artificial Sequence
<220> FEATURE:
<223> OTHER INFORMATION: Synthetic nucleotide (SPIR alpha linker R)

<400> SEQUENCE: 16
aaaaagcttt caaccgcagc caccgcc                                         27

<210> SEQ ID NO 17
<211> LENGTH: 27
<212> TYPE: RNA
<213> ORGANISM: Artificial Sequence
<220> FEATURE:
<223> OTHER INFORMATION: Synthetic siRNA_DNA
<220> FEATURE:
<221> NAME/KEY: misc_feature
<222> LOCATION: (26)..(27)
<223> OTHER INFORMATION: 26th and 27th nucleotide sequences are DNA c
      and DNA a

<400> SEQUENCE: 17
gggauauuaa uacuacuuca guacann                                         27

<210> SEQ ID NO 18
<211> LENGTH: 24
<212> TYPE: RNA
<213> ORGANISM: Artificial Sequence
```

-continued

```
<220> FEATURE:
<223> OTHER INFORMATION: Synthetic siRNA ansti sense

<400> SEQUENCE: 18
uguacugaag uauuaauauc cccg                                        24

<210> SEQ ID NO 19
<211> LENGTH: 50
<212> TYPE: DNA
<213> ORGANISM: Artificial Sequence
<220> FEATURE:
<223> OTHER INFORMATION: HPRT gene primer

<400> SEQUENCE: 19
ggctataagt tctttgctga cctgcrgctt gcaaccttaa ccattttggg            50

<210> SEQ ID NO 20
<211> LENGTH: 40
<212> TYPE: DNA
<213> ORGANISM: Artificial Sequence
<220> FEATURE:
<223> OTHER INFORMATION: CD47 gene primer

<400> SEQUENCE: 20
aggagaaaag cccgtgaagr tggcaatggt gaaagaggtc                        40
```

IMMUNOREGULATORY PROTEIN-SIRNA COMPLEX HAVING ANTICANCER ACTIVITY

CROSS-REFERENCE TO RELATED APPLICATIONS

This application claims, under 35 U.S.C. § 119, the priority of Korean Patent Application No. 10-2019-0085912 filed on Jul. 16, 2019 in the Korean Intellectual Property Office, the disclosure of which is incorporated herein by reference in its entirety.

SEQUENCE LISTING

This application contains a Sequence Listing submitted via EFS-Web and hereby incorporated by reference in its entirety. The Sequence Listing is named SEQCRF-CHIP-156-KIST.txt, created on Nov. 6, 2019, and 12,883 bytes in size.

TECHNICAL FIELD

The present disclosure relates to an immunoregulatory protein-siRNA complex having anticancer activity, more particularly to an immunoregulatory protein-siRNA complex which induces death of cancer cells by inhibiting the immune escape mechanism of the cancer cells, thereby enhancing phagocytosis by macrophages.

BACKGROUND

Cancer has been the number one cause of death over the past few years. A variety of technologies have been developed to treat cancer. For example, anticancer drugs such as doxorubicin or paclitaxel are effective in inhibiting the growth of cancer cells or killing them. However, the anticancer drugs exhibit toxicity to cancer cells and normal cells alike. Therefore, despite their anticancer effects, they are not suitable to be used for treatment due to severe side effects.

In order to solve this problem, development of anticancer drugs using siRNAs is actively ongoing. siRNA is known to interfere with the expression of specific target genes. Therefore, it is expected that a drug having superior anticancer effect with minimized side effect can be developed if the function of siRNA is utilized. In this regard, siRNAs targeting oncogenes, immune cells and various genes such as tumor microenvironment regulators have been developed. However, siRNA is disadvantageous in that it cannot exist stably in vivo on its own and the effect of delivery into cells is very low.

To solve this problem, nanoparticles using various materials such as liposome, chitosan nanoparticle, PLGA (poly(lactic-co-glycolic acid)), etc. have been studied as a carrier for delivering siRNA. Although the nanoparticles can improve stability and delivery as compared to when siRNA is used alone, they may induce toxicity in vivo because the nanoparticles themselves are foreign materials. In addition, they are problematic in that the efficiency of gene transfection is very low because they are degraded by endosomes/lysosomes after being introduced into cells. Accordingly, the recent researches are focused on various substances existing in the body (proteins, exosomes, antibodies, etc.) as carriers in order to effectively deliver siRNA into cancer cells with reduced toxicity. Despite these efforts, commercialization is not achieved yet due to the problems of delivery efficiency and mechanism. For example, the exosome is limited in effectively delivering a drug because it is easily degraded and broken down in vivo, and the antibody has the problem that it cannot effectively deliver siRNA into cells because of relatively large size.

REFERENCES OF THE RELATED ART

Patent Documents (Patent document 1) Patent document 1. Korean Patent Registration No. 10-1977532.
(Patent document 2) Patent document 2. Korean Patent Publication No. 10-2018-0134424.

SUMMARY

The present disclosure is directed to providing a fusion protein-siRNA complex having superior anticancer activity, which is delivered specifically into cancer cells via cancer cell receptors and enhances phagocytosis by macrophages by doubly inhibiting the immune escape mechanism of the cancer cells.

The present disclosure is also directed to providing a composition for treating or preventing cancer, which contains the fusion protein-siRNA complex as an active ingredient.

The present disclosure provides a fusion protein-siRNA complex, which contains an immunoregulatory fusion protein (A); and a siRNA (B), wherein the immunoregulatory fusion protein (A) is one in which SIPRα protein is bound to a linker peptide cleaved by a lysosomal degradative enzyme.

The SIPR protein may be represented by any one of SEQ ID NOS: 3, 5, 7, 9 and 11, and the linker peptide may be represented by SEQ ID NO: 13.

The immunoregulatory fusion protein (A) may be represented by SEQ ID NO: 1.

The siRNA may be CD47 siRNA.

The siRNA represented by SEQ ID NO: 17 or 18.

The fusion protein-siRNA complex may have an average molecular weight of 20-60 kDa.

The present disclosure also provides a pharmaceutical composition for treating or preventing cancer, which contains the fusion protein-siRNA complex as an active ingredient.

The cancer may be one or more selected from a group consisting of brain tumor, spinal cord tumor, retinoblastoma, oral cancer, nasal cavity cancer, paranasal sinus cancer, pharyngeal cancer, laryngeal cancer, neck cancer, head and neck cancer, melanoma, skin cancer, breast cancer, thyroid cancer, malignant adrenal tumor, endocrine cancer, lung cancer, pleural tumor, respiratory tract cancer, esophageal cancer, stomach cancer, small intestine cancer, colon cancer, anal cancer, liver cancer, biliary tract cancer, pancreatic cancer, kidney cancer, bladder cancer, prostate cancer, testicular cancer, penile cancer, cervical cancer, endometrial cancer, choriocarcinoma, ovarian cancer, blood cancer including acute/chronic leukemia, malignant lymphoma and multiple myeloma, bone tumor, soft tissue tumor, childhood leukemia and childhood cancer.

The present disclosure also provides a method for treating cancer in a human or a non-human animal, comprising administering to a subject in need of such treatment a therapeutically effective amount of a fusion protein-siRNA complex.

The fusion protein-siRNA complex according to the present disclosure is absorbed into cancer cells via receptors specifically overexpressed in the cancer cells, and has maximized anticancer activity by doubly regulating the immune defense function of the cancer cells. In addition, it is advantageous in that it has low cytotoxicity and few side effects due to high delivery efficiency.

Also, it is less risky to the body because it causes the cancer cells to be removed by the autoimmunity (macrophage phagocytosis) of the patient by inhibiting the immunity of the cancer cells, rather than directly inducing the death of the cancer cells.

DETAILED DESCRIPTION OF EMBODIMENTS

Hereinafter, various aspects and exemplary embodiments of the present disclosure will be described in more detail.

The inventors of the present disclosure have intended to prepare a complex which exhibits no cytotoxicity or activity at all in normal state but exhibits toxicity or activity after being delivered into specific cells (cancer cells). For this, the greatest concern was to be degraded by lysosomes existing in the cells after delivery into the cells to exhibit activity. They have tested numerous materials which have superior cancer cell targeting ability and intracellular delivery ability but exhibit little cytotoxicity. As a result, they have identified that a fusion protein-siRNA complex according to the present disclosure is delivered specifically to cancer cells with high intracellular delivery efficiency and exhibits a remarkable effect of enhancing phagocytosis of the cancer cells by macrophages as it is degraded by lysosomes in the cells, and have completed the present disclosure.

Figure 1:
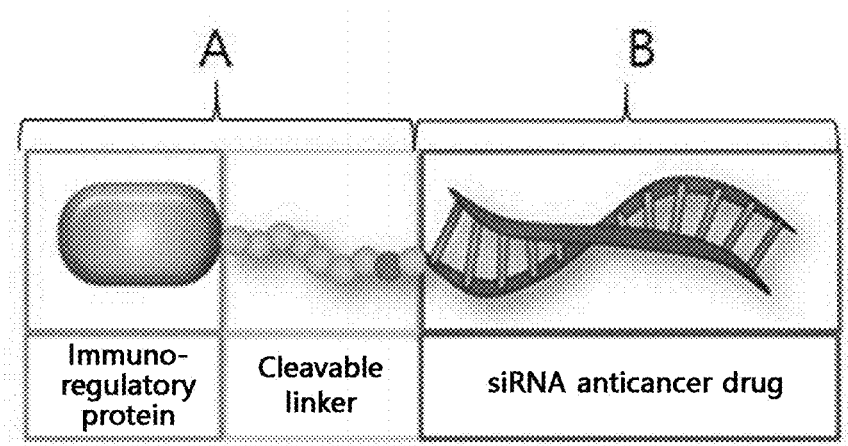
FIG. 1 schematically shows the structure of a fusion protein-siRNA complex.

An aspect of the present disclosure relates to a fusion protein-siRNA complex including an immunoregulatory fusion protein (A); and a siRNA (B), wherein the immunoregulatory fusion protein (A) is one in which SIPRα protein is bound to a linker peptide cleaved by a lysosomal degradative enzyme. Its structure is schematically shown in FIG. 1.

The fusion protein-siRNA complex according to the present disclosure enters cancer cells by specifically reacting with the cells and can be activated as they are spontaneously cleaved by lysosomes in the cells.

The SIPRα protein may contain any one of amino acid sequences represented by SEQS ID NOS: 3, 5, 7, 9 and 11.

For easy construction of a protein-siRNA complex, the fusion protein is designed such that the thiol group of the protein is bound to siRNA in a one-to-one ratio by inserting the cysteine amino acid to the C-terminal of the immunoregulatory fusion protein. This solves the problems of inter-particle heterogeneity, difficulty of analysis and difficulty of quality control that may occur due to simple random binding between a protein and a siRNA, and allows formation of a well-defined, simple structure (fusion protein-siRNA complex). Therefore, the fusion protein-siRNA complex of the present disclosure may exhibit an effect favorable for clinical application due to this structural characteristics as compared to random fusion protein-siRNA complexes.

The linker peptide is not specially limited as long as it is a sequence that can be easily cleaved by the enzymes existing in lysosomes. It may consist of specifically 5-15, more specifically 7-12, amino acids. Most specifically, it may contain an amino acid sequence represented by SEQ ID NO: 13.

The linker peptide that is cleaved by the lysosomal degradative enzyme may contain an amino acid sequence represented by SEQ ID NO: 13 (GFLG). It may be cleaved by the cathepsin B enzyme present in the lysosomes and may facilitate endosomal escape via receptor-mediated endocytosis of the fusion protein after the cellular uptake. Degradation in the endosomes is a big obstacle for a siRNA carrier, and overcoming this improves the efficiency of introduction (transfection) of genes into cells.

In addition, immunogenic cell death (ICD) enhances immune response by inducing damage-associated molecular pattern (DAMP) upon cell death. By doubly regulating the same target, a combination of the immunoregulatory fusion protein and the siRNA can provide much enhanced effect as compared to the protein and the siRNA alone.

In the present disclosure, the 'siRNA (short interfering RNA)' refers to a double-stranded RNA that can induce RNAi which inhibits the activity of a gene. In the present disclosure, the siRNA means a siRNA that can inhibit the activity of CD47. However, the siRNA may be any one as long as it can induce RNAi. For example, a siRNA obtained by chemical synthesis, biochemical synthesis or biosynthesis, a double-stranded RNA of about 10 or more base pairs formed as a double-stranded RNA of about 40 or more base pairs is degraded in vivo, etc., can be used.

The siRNA may consist of a sequence having about 70% or higher, specifically 75% or higher, more specifically 80% or higher, or higher specifically 85% or higher, or higher specifically 90% or higher, particularly specifically 95% or higher, most specifically 100%, of homology for a part of the nucleic acid sequence of CD47. A RNA including a double-stranded portion or a variant thereof may also be used. The sequence portion having homology is commonly at least 20 nucleotides, specifically about 23-30 nucleotides, in length. In addition, the siRNA may specifically consist of a base sequence that can bind complementarily to a region of the least homology with other RNAs from the base sequence of CD47.

The fusion protein-siRNA complex according to the present disclosure has remarkably high intracellular delivery efficiency and also has remarkably high anticancer activity as compared to when siRNA is administered alone.

In addition, because the fusion protein-siRNA complex is easily dissolved in a physiological solution, it is absorbed easily and exhibits excellent bioavailability.

The base sequence of the siRNA is not specially limited as long as it can silence the CD47 gene and inhibit the expression of the CD47 gene. Specifically, SEQ ID NO: 17 or 18 may be used in terms of the silencing effect, and maleimide may be bound to the 3'-end of the siRNA.

Figure 2:
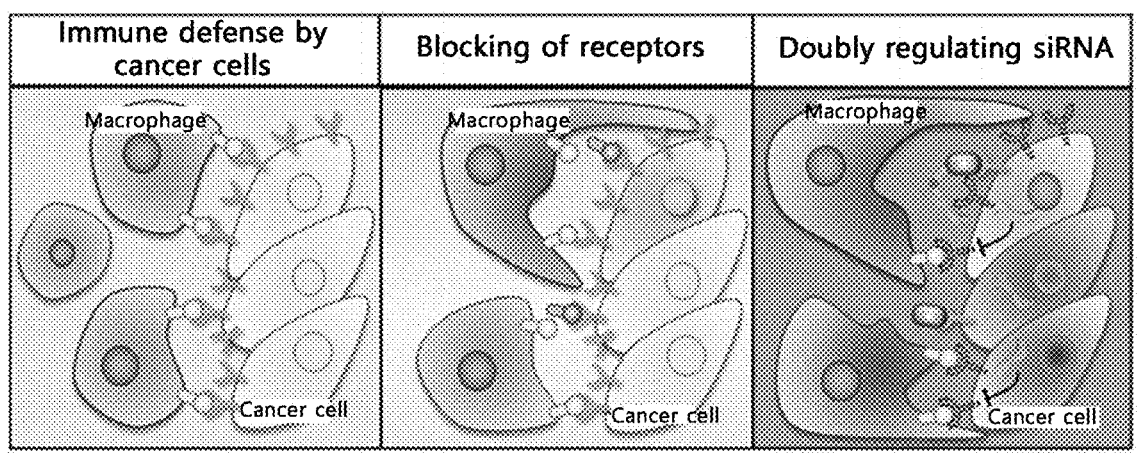
FIG. 2 schematically shows the action mechanism of a fusion protein-siRNA complex. It maximizes cancer immunotherapy efficiency because an immunoregulatory protein and a siRNA anticancer drug doubly regulating the same receptors of cancer cells in 1) protein level and 2) mRNA level.
Figure 3:
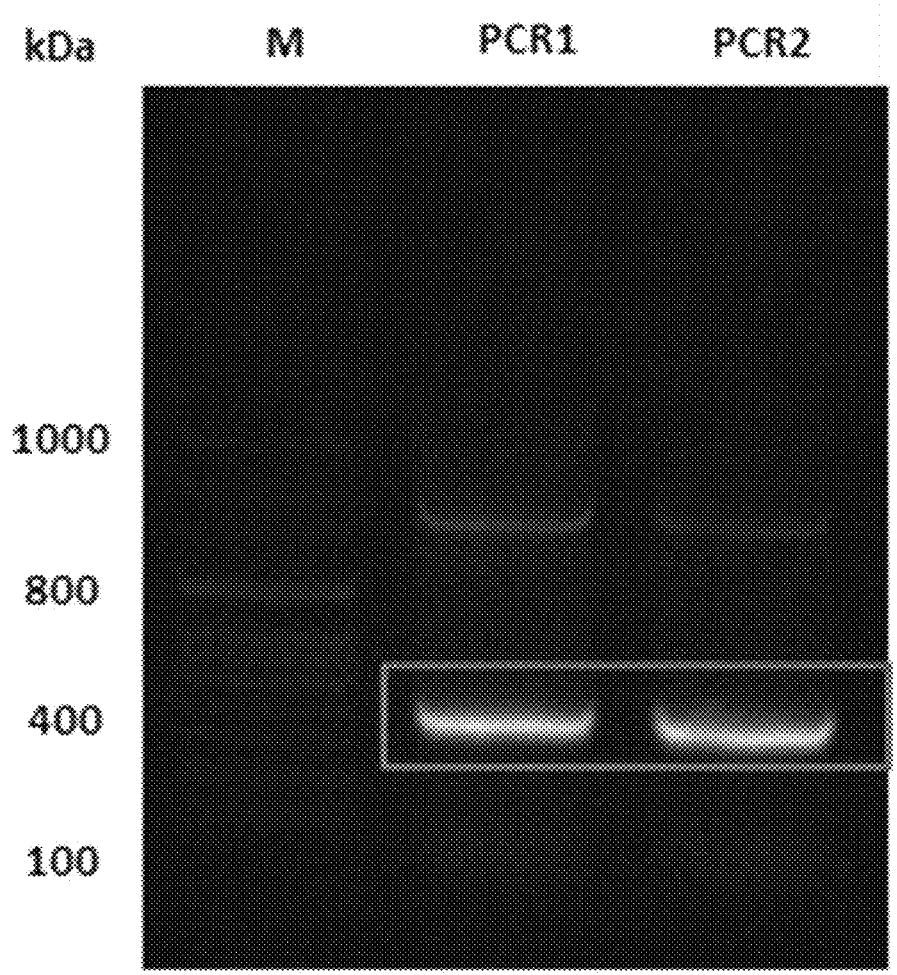
FIG. 3 shows a result of obtaining a colony from a selected transformant prepared in Example 1, conducting PCR, and performing analysis using a gel image (gel documentation) system.
Figure 4:
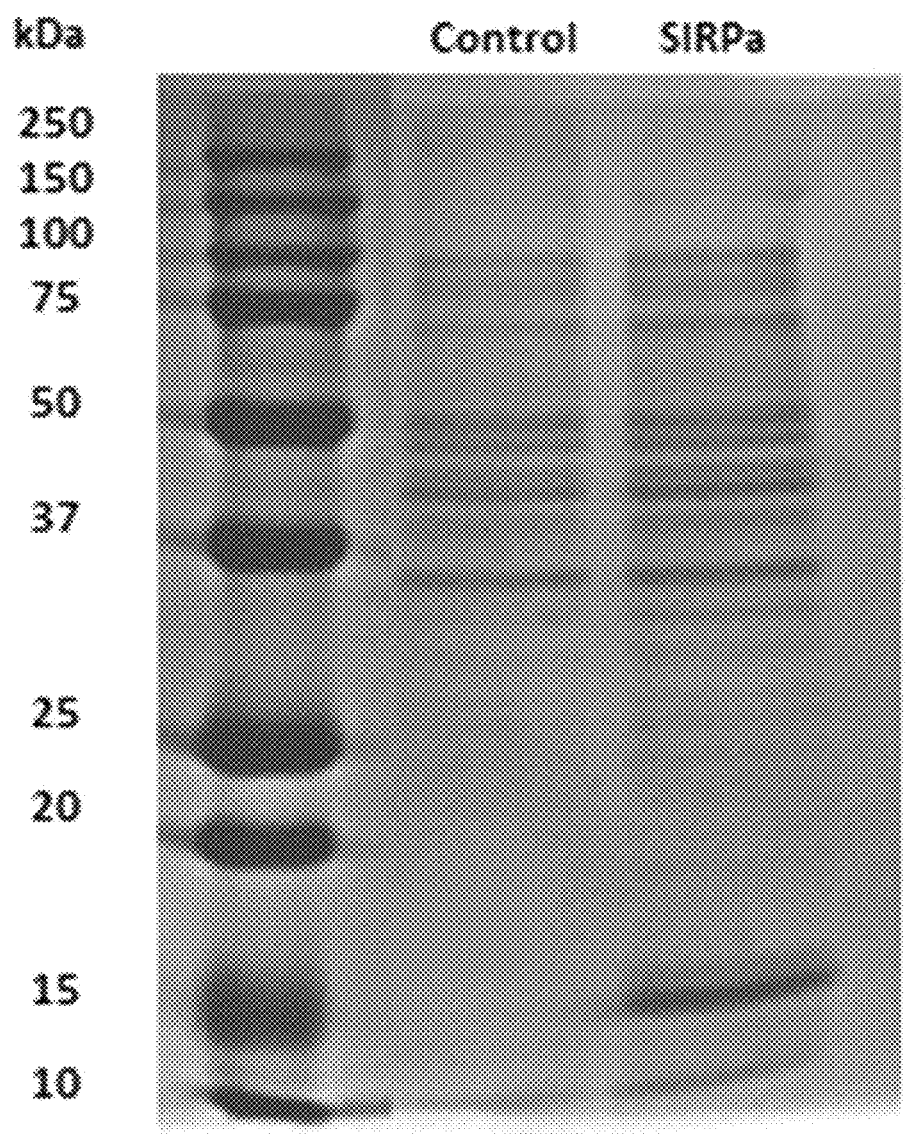
FIG. 4 shows a result of identifying the binding of a fusion protein separated and purified in Example 1 using a SDS-PAGE gel. Lane 1 shows a result for a control group (control), and lane 2 shows a result for the fusion protein (SIRPα-linker).
Figure 5:
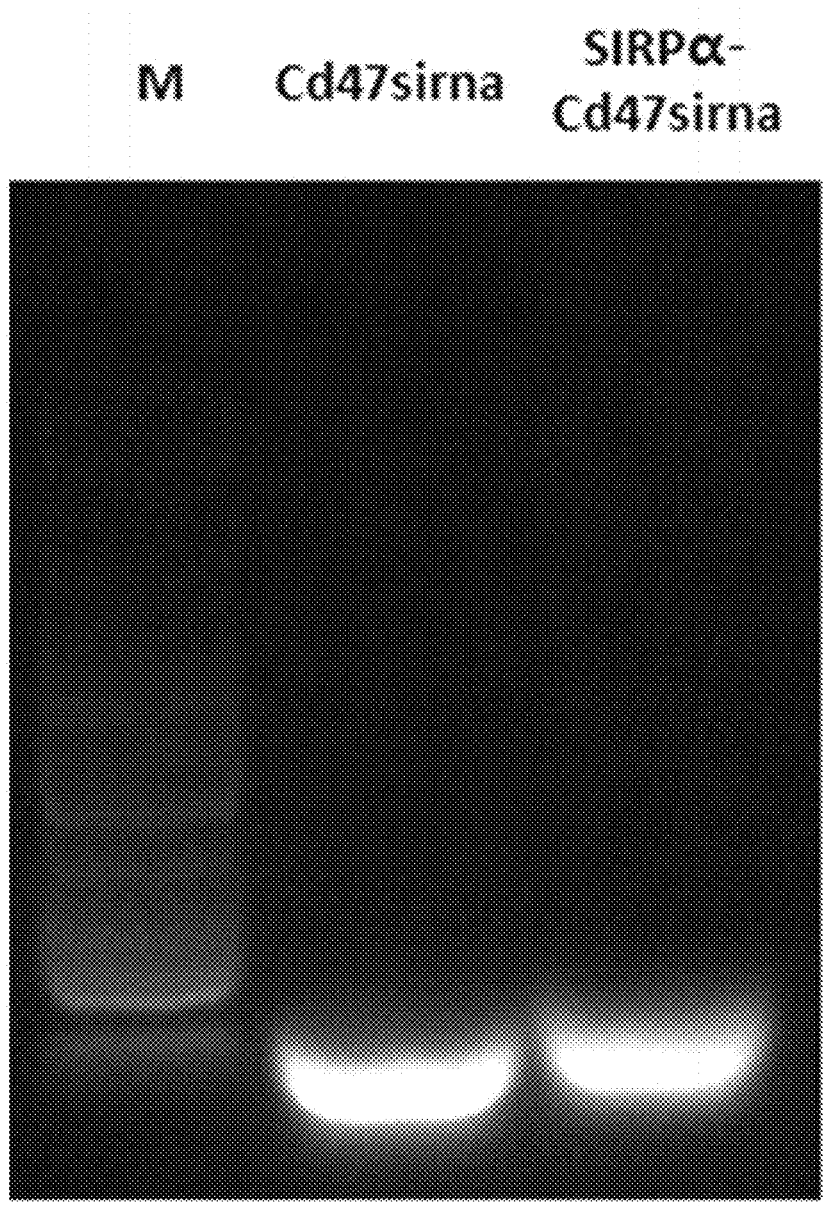
FIG. 5 shows a result of identifying a fusion protein-siRNA separated and purified in Example 2 using an agarose gel.

Because the fusion protein-siRNA complex according to the present disclosure binds to receptors expressed specifically in cancer cells, it exhibits high cancer cell-specific delivery efficiency. In addition, the fusion protein-siRNA complex inhibits the immunity of cancer cells by binding to CD47 receptors, silencing the CD47 gene after being degraded in the cancer cells, etc. and, thereby, allows macrophages to attack the cancer cells via phagocytosis. That is to say, because the fusion protein-siRNA complex according to the present disclosure inhibits the immunity of the cancer cells such that macrophages can remove the cancer cells, unlike the existing anticancer drugs or carriers, it induces anticancer effect through autoimmunity rather than killing the cancer cells on its own. The action mechanism of the fusion protein-siRNA complex is schematically shown in FIG. 2.

It was confirmed through various experiments that the fusion protein-siRNA complex of the present disclosure binds specifically to cancer cells, is delivered into the cells, and enhances phagocytosis by macrophages by inhibiting the immunity of the cancer cells, so that the cancer cells can be removed.

Another aspect of the present disclosure relates to a pharmaceutical composition for treating or preventing cancer, which contains the fusion protein-siRNA complex as an active ingredient.

The present disclosure also relates to a veterinary pharmaceutical composition for treating or preventing cancer, which contains the fusion protein-siRNA complex as an active ingredient.

In addition, the present disclosure provides a method for treating cancer by administering the composition to human or a non-human animal.

In addition, the present disclosure provides a method for inhibiting the immune response of cancer cells observed in a cancer patient, which includes administering the fusion protein-SiRNA complex of an effective for inhibiting the immune response of the cancer cells to human or a non-human mammal.

In addition, the present disclosure provides a novel use of the fusion protein-siRNA complex for preparation of a drug for treating or preventing cancer or a veterinary drug.

It was confirmed that the fusion protein-siRNA complex according to the present disclosure can be administered through various routes and provides remarkably (1.5-5 times) superior pharmacological effect on cancer cells as compared to when the fusion protein or the siRNA is administered alone.

Specifically, the complex of the present disclosure can be specifically delivered into cancer cells easily and exhibits very superior potential stability as compared to when the siRNA or the SIPRα protein is used alone. In addition, it is very stable because it is free from the risk of uncontrolled replication and there is no concern of interference due to transfection or potential side effects since it is not necessary to use a viral or non-viral vector for delivery of the siRNA. In addition, it is greatly advantageous economically because it can be synthesized at very low cost as compared to when a carrier such as a vector is used and also exhibits very superior delivery efficiency (maximum preventive or therapeutic effect can be achieved by administering the siRNA and the SIPRα protein at low concentrations).

Topical treatment (e.g., anticancer drug) to kill specific cancer cells is not effective and risky to the body. However, the complex of the present disclosure is greatly advantageous in that it is less risky to the body because the cancer cells are removed by autoimmunity by inhibiting the immunity of the cancer cells and superior anticancer effect can be provided with little side effect.

The cancer refers to common cancer. The cancer may be head and neck cancer including brain tumor, spinal cord tumor, retinoblastoma, oral cancer, nasal cavity cancer, paranasal sinus cancer, pharyngeal cancer, laryngeal cancer or neck cancer, skin cancer including melanoma, breast cancer, thyroid cancer, malignant adrenal tumor, respiratory tract cancer, endocrine cancer, lung cancer, pleural tumor, cancer of the digestive system including esophageal cancer, stomach cancer, malignant tumor of the small intestine, colon cancer, anal cancer, liver cancer, biliary tract cancer or pancreatic cancer, urologic cancer including kidney cancer, bladder cancer, prostate cancer, testicular cancer or penile cancer, gynecologic cancer including cervical cancer, endometrial cancer, choriocarcinoma or ovarian cancer, blood cancer including acute or chronic leukemia, malignant lymphoma or multiple myeloma, bone or soft tissue tumor including bone tumor or soft tissue tumor, childhood cancer including childhood leukemia or pediatric solid tumor, etc. It also includes recurrent cancer. The recurrent cancer means a cancer that has recurrent after cancer treatment.

In the present disclosure, the "complex" refers to a covalent complex which contains a fusion protein and a siRNA described below, which are bonded through genetic fusion or chemical bonding.

The "genetic fusion" refers to linear covalent linkage formed through genetic expression by a DNA sequence encoding a protein.

The chemical bonding is not specially limited and may be one commonly used in the art. Specifically, it may refer to binding a derivative containing a maleimide group to the end of a siRNA using a linker, in order to bind the cysteine residue of a fusion protein to the siRNA, and then forming a bond by reacting the thiol of the cysteine residue present in the fusion protein with the maleimide group of the siRNA.

When preparing the fusion protein-siRNA complex by mixing the fusion protein with the siRNA, the mixing ratio may be specifically 1:1-10. If the ratio is below 1:1, the complex is not formed appropriately and the delivery efficiency to cancer cells is low.

It was confirmed that, when the fusion protein-siRNA complex was administered, the delivery efficiency to cancer cells was increased and the effect of enhancing macrophage phagocytosis was remarkable (1.5-3 times or higher) as compared to when only the siRNA (CD47 siRNA) or the SIPRα protein was administered.

The pharmaceutical composition of the present disclosure may be one formulated into a pharmaceutical composition by including one or more pharmaceutically acceptable carrier in addition to the active ingredient described above.

When the composition is formulated as a liquid solution, one or more of saline, sterile water, Ringer's solution, buffered saline, albumin solution for injection, dextrose solution, maltodextrin solution, glycerol and ethanol may be used as a sterile and bioavailable pharmaceutically acceptable carrier. If necessary, other common additives such as an antioxidant, a buffer, a bacteriostat, etc. may be added.

The pharmaceutical composition for treating or preventing cancer may be prepared by using a pharmaceutically acceptable and physiologically acceptable adjuvant in addition to the active ingredient. As the adjuvant, an excipient, a disintegrant, a sweetener, a binder, a coating agent, a swelling agent, a lubricant, a glidant, a flavorant or a solubilizer may be used.

The pharmaceutical composition for treating or preventing cancer of the present disclosure may be formulated into an injection formulation such as an aqueous solution, a suspension, an emulsion, etc., a pill, a capsule, a granule or a tablet by additionally adding a diluent, a dispersant, a surfactant, a binder or a lubricant. In addition, it may be prepared into a suitable formulation depending on the corresponding disease or ingredients using the method described in Remington's Pharmaceutical Science, Mack Publishing Company, Easton Pa.

Because the pharmaceutical composition for treating or preventing cancer of the present disclosure targets the receptors of cancer cells and has specificity for the cancer cells, its administration route is not specially limited. Specifically, it can be administered according to a common method via intravenous, intraarterial, intraabdominal, intramuscular, intraperitoneal, intrasternal, transdermal, intranasal, inhalatory, topical, rectal, oral, intraocular or intradermal route, most specifically via intravenous injection, although not being specially limited thereto. Depending on purposes, it may be administered intraperitoneally, intramuscularly, subcutaneously, orally, intranasally, intrapulmonarily or intrarectally.

The 'pharmaceutical composition', 'drug', 'veterinary pharmaceutical composition' or 'veterinary drug' may further contain, in addition to the fusion protein-siRNA complex as the active ingredient, a suitable carrier, excipient or diluent commonly used in the preparation of a pharmaceutical composition, etc.

The 'carrier' is a compound that facilitates inclusion of a compound into cells or tissues. The 'diluent' is a compound which stabilizes the biologically active form of a target compound and dilutes the compound dissolved in water.

The carrier, excipient or diluent that may be contained in the pharmaceutical composition of the present disclosure may be lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate or mineral oil. For formulation, a commonly used diluent or excipient such as a filler, an extender, a binder, a wetting agent, a disintegrant, a surfactant, etc. is used.

The term "administration" used in the present disclosure refers to provision of the composition of the present disclosure to a subject according to an adequate method.

The dosage of the pharmaceutical composition, drug, veterinary pharmaceutical composition or veterinary drug may vary depending on the age, sex or body weight of a patient or an animal to be treated. Above all, it will depend on the state of the subject to be treated, the particular category or class of the target disease, administration route, or the property of the therapeutic agent used.

The administration dosage of the pharmaceutical composition, drug, veterinary pharmaceutical composition or veterinary drug can be selected adequately depending on the absorption rate of the active ingredient in vivo, excretion rate, the age, body weight, sex and condition of a patient or an animal to be treated, the severity of a disease to be treated, etc. A daily administration dosage may be 0.0001-1,000 mg/kg, specifically 0.001-500 mg/kg, more specifically 0.001-250 mg/kg, in general. A single-dose unit may be administered at regular time intervals if necessary.

The pharmaceutical composition, drug, veterinary pharmaceutical composition or veterinary drug may be administered either alone or in combination with another preventive or therapeutic agent, either sequentially or simultaneously.

The method for treating cancer includes administration of the composition to human or a non-human animal, particularly a mammal, for example, a subject with a cancer disease.

The cancer refers to common cancer. The cancer may be head and neck cancer including brain tumor, spinal cord tumor, retinoblastoma, oral cancer, nasal cavity cancer, paranasal sinus cancer, pharyngeal cancer, laryngeal cancer or neck cancer, skin cancer including melanoma, breast cancer, thyroid cancer, malignant adrenal tumor, respiratory tract cancer, endocrine cancer, lung cancer, pleural tumor, cancer of the digestive system including esophageal cancer, stomach cancer, malignant tumor of the small intestine, colon cancer, anal cancer, liver cancer, biliary tract cancer or pancreatic cancer, urologic cancer including kidney cancer, bladder cancer, prostate cancer, testicular cancer or penile cancer, gynecologic cancer including cervical cancer, endometrial cancer, choriocarcinoma or ovarian cancer, blood cancer including acute or chronic leukemia, malignant lymphoma or multiple myeloma, bone or soft tissue tumor including bone tumor or soft tissue tumor, childhood cancer including childhood leukemia or pediatric solid tumor, etc. It also includes recurrent cancer. The recurrent cancer means a cancer that has recurrent after cancer treatment.

The dosage, method and number of administration for the treatment may be determined in consideration of the dosage, method and number of administration of the pharmaceutical composition, drug, veterinary pharmaceutical composition or veterinary drug.

Hereinafter, the present disclosure will be described in more detail through examples. However, the following examples are for illustrative purposes only and not intended to limit the scope of this disclosure.

Example 1. Preparation of Immunoregulatory Fusion Protein Wherein SIPRα Protein is Fused with Linker Peptide Cleaved by Lysosomal Degradative Enzyme (SIPRα-Linker)

First, in order to construct a vector for expressing an immunoregulatory fusion protein, a vector containing a gene (SEQ ID NO: 2) encoding an immunoregulatory fusion protein (SEQ ID NO: 1) was synthesized through Cosmo Genetech (Seoul, South Korea). PCR (polymerase chain reaction) was conducted using the vector as a template and using the primers described in Table 1. As a result, a gene (SEQ ID NO: 2) into which an immunoregulatory fusion protein in which a gene (GGT GGC TTT CTG GGT GGC GGT GGC TGC GGT; SEQ ID NO: 14) encoding a linker peptide (SEQ ID NO: 13) is fused with a gene (SEQ ID NO: 4) encoding an immunoregulatory protein (SIRPα protein) (SEQ ID NO: 3) is introduced was obtained. An expression vector was prepared by inserting the amplified immunoregulatory fusion protein gene into the Nde1 and HindIII restriction enzyme sites of the pet28a vector.

Fusion proteins were prepared using a variant SIRPα protein represented by SEQ ID NO: 3, a wild-type SIRPα protein represented by SEQ ID NO: 5, a wild-type SIRPg protein represented by SEQ ID NO: 7, a SIRPg variant 1 protein represented by SEQ ID NO: 9 or a SIRPg variant 2 represented by SEQ ID NO: 11 instead of the immunoregulatory protein (A) represented by SEQ ID NO: 3. It was confirmed that fusion proteins were prepared actually.

TABLE 1

| Primer | SEQ ID NO | Sequence (5' → 3') |
| --- | --- | --- |
| SPIRα_linker-F | SEQ ID NO 15 | AAA CAT ATG GAA GAG GAG CTG CAG |
| SPIRα_linker-R | SEQ ID NO 16 | AAA AAG CTT TCA ACC GCA GCC ACC GCC |

The His-tag allows purification and identification of a protein attached to the C-terminal of the expressed fusion protein as the gene is expressed as the fusion protein. After obtaining genes using SEQ ID NOS: 7 and 8, a pET-His expression vector was prepared by inserting them into the Nde1 and HindIII restriction enzyme sites of the pet28a vector.

Then, *E. coli* BL21 (DE3, Novagen) was prepared into competent cells using a CaCl$_2$ buffer. Subsequently, the competent cells were transformed with each expression vector by a heat shock method of leaving the cells at 42° C. for 2 minutes. From the transformants, the transformant expressing the fusion protein was selected and cultured for 12 hours in an incubator at 30° C. Then, the cultured transformant was centrifuged at 4,000 g for 10 minutes, and the cells were recovered from pellets remaining after removing the supernatant. The recovered cells were lysed using a sonicatior. After centrifuging the obtained cell lysate at 4° C. and 14,000 rpm for 20 minutes, an overexpressed fusion protein having an amino acid sequence of SEQ ID NO: 1 was separated from the supernatant by fast protein liquid chromatography (Bio-Rad Laboratories, USA) equipped with an IMAC Kit His tag adsorption column (Bio-Rad Laboratories, USA).

Example 2. Preparation of Fusion Protein-siRNA Complex

A siRNA (CD47 siRNA) with a sense strand having a sequence of 5'-GGG AUA UUA AUA CUA CUU CAG UAC A*C*A (*DNA)-3' (SEQ ID NO: 17) and an antisense strand having a sequence of 5'-UGU ACU GAA GUA UUA AUA UCC CCG-3' (SEQ ID NO: 18) was purchased from Mbiotech (IDT Korea, Gyeonggi, South Korea). In the SEQ ID NO: 17, the 26th and 27th base sequences are DNA.

Maleimide was introduced at the 3'-end of the sense strand of the obtained siRNA so that the siRNA and the fusion protein (Example 1) could form a complex. Specifically, after reacting the siRNA and maleimide-NHS in a pH 8.3. 0.1 M HEPES buffer for 4 hours, only the siRNA was purified using a NAP column and then freeze-dried.

After adding the maleimide-introduced siRNA to the fusion protein prepared in Example 1 at a molar ratio of 1:1 in a HEPES buffer (pH 7.4), a fusion protein-siRNA complex obtained by purifying using 30K Amicon tube.

The maleimide introduced into the siRNA and the thiol group of cysteine present at the end of the fusion protein are bound 1:1 to form a fusion protein-siRNA complex. The fusion protein-siRNA complex was purified using a NAP-10 column and then freeze-dried.

Test Example 1. Confirmation of Expression of Fusion Protein (SIPRα-Linker)

After extracting a colony from the transformant selected in Example 1, PCR was conducted using the primers of Table 1. The obtained PCR product was analyzed with a gel image system (Geldoc-it 300, UVP, CA, USA). The identified band was confirmed to correspond to that of the gene sequence of about 400 bp.

And, the fusion protein separated and purified in Example 1 was diluted with a buffer for SDS-PAGE (0.5 M Tris-[0113] HCl (pH 6.8), 10% glycerol, 5% SDS, 5% β-mercaptoethanol, 0.25% bromophenol blue), denatured by boiling at 100° C. for 15 minutes and then electrophoresed on 15% SDS-PAGE gel.

FIG. 3 shows the result of separating DNA from the transformant selected in Example 1, conducting PCR, and performing analysis using a gel image (gel documentation) system. It was confirmed that the gene encoding the fusion protein was successfully inserted in the transformant.

FIG. 4 shows the SDS-PAGE result of the fusion protein separated and purified in Example 1. Lane 1 shows a result for a control group (control) with no expression vector added, and lane 2 shows a result for the fusion protein (SIPRα-linker). It was confirmed that the fusion protein was expressed normally by the expression vector.

Test Example 2. Confirmation of Synthesis of Fusion Protein-siRNA Complex

It was investigated whether the fusion protein-siRNA complex was successfully synthesized in Example 2.

FIG. 5 shows a result of identifying the bonding of the fusion protein-siRNA separated and purified in Example 2 on 1% agarose gel after staining with the 6×DNA gel loading dye (Thermo Scientific, Mass., USA). Lane 1 shows a result for CD47 siRNA as a control group (control), and lane 2 shows a result for the fusion protein-siRNA complex (SIRPα-CD47 siRNA). It was confirmed that the fusion protein-siRNA complex was formed successfully.

Test Example 3. Analysis of Enzyme Specificity of Fusion Protein-siRNA Complex

It was investigated whether the fusion protein-siRNA complex prepared in Example 2 is cleaved by a lysosomal degradative enzyme as desired. First, the fusion protein-siRNA complex prepared in Example 2 was treated with the papain enzyme and HPLC (high-performance liquid chromatography) was carried out after conducting enzymatic reaction at room temperature for 10 minutes.

The sample for HPLC was obtained by purifying and concentrating the fusion protein-siRNA complex prepared in Example 2 with the 30K Amicon tube (Merck Millipore, Miss., USA). After adsorbing the sample to a C18 column (Xbridge C18, Waters, Miss., USA), it was analyzed by HPLC (Agilent Technologies, Calif., USA) while eluting for 30 minutes with concentration gradients using 0.1% TFA/ 5-95% ACN solutions. As a control group, the fusion protein-siRNA complex prepared in Example 2, not treated with the papain enzyme, was used.

Figure 6:
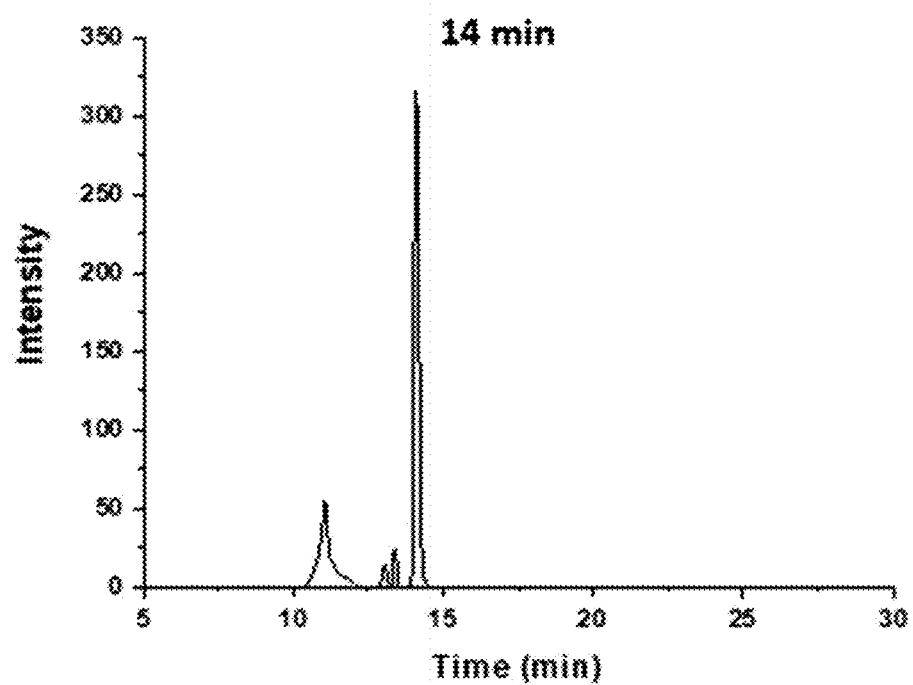
FIG. 6 shows a result of analyzing a fusion protein-siRNA separated and purified in Example 2 by HPLC.
Figure 7:
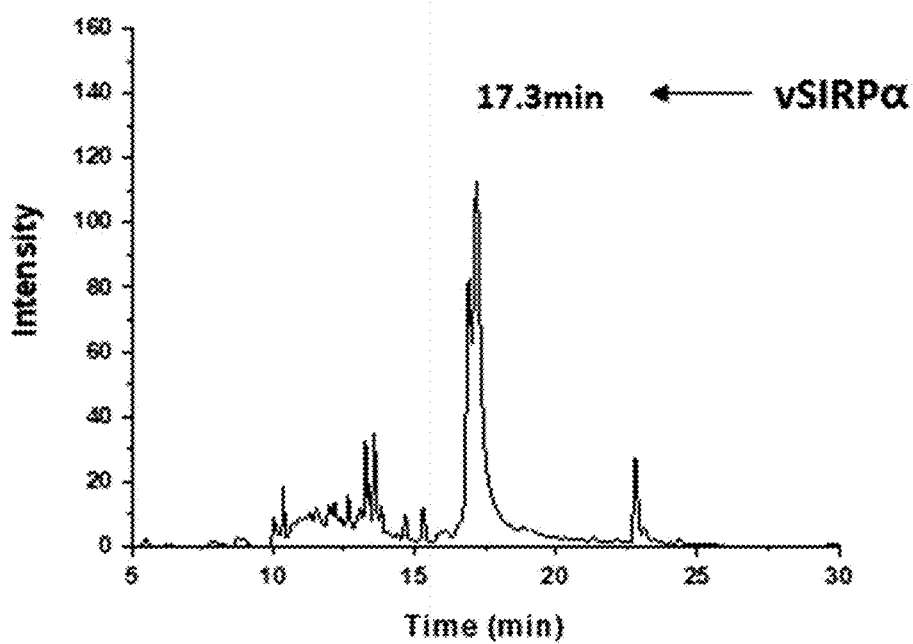
FIG. 7 shows a result of treating a fusion protein-siRNA separated and purified in Example 2 with the papain enzyme and analyzing the same by HPLC.

FIG. 6 shows a result of analyzing the fusion protein-siRNA separated and purified in Example 2 by HPLC, and FIG. 7 shows a result of treating the fusion protein-siRNA separated and purified in Example 2 with the papain enzyme and analyzing the same by HPLC.

As seen from FIG. 6 and FIG. 7, the SIRPα protein was not detected in the fusion protein-siRNA separated and purified in Example 2 but was detected after treating with the papain enzyme. Through this, it can be seen that the SIRPα protein is released as the linker peptide present in the fusion protein-siRNA separated and purified in Example 2 is cleaved by the papain enzyme.

Test Example 4. Confirmation of Intracellular Delivery Ability of Fusion Protein-siRNA Complex It was investigated whether the fusion protein-siRNA complex prepared in Example 2 is effectively taken up into cells in vitro. First, 2×10$^5$ HT-29 cells, which are human-derived colon cancer cells, were seeded onto a 35-mm cover glass bottom dish. Then, after adding SIRPα protein (SIRPα), CD47 siRNA or the fusion protein-siRNA complex prepared in Example 2 (SIPRα-CD47 siRNA), the cells were cultured at 37° C. for a day. Then, CD47 SiRNA was stained red by using the TOTO3 stain. Next, after treating with the fusion protein-siRNA complex separated and purified in Example 2 at a concentration of 100 pmol/mL, the cells were cultured for 4 hours in a carbon dioxide incubator at 37° C. Then, the cells were treated with a fixative and the SIRPα protein was stained green using FITC-labeled His-tag antibody. After staining the nuclei of the cells by treating with a 4',6-diamidino-2-phenylindole (DAPI) solution for 10 minutes, fluorescence was measured by confocal microscopy.

A mixture solution of the fusion protein-siRNA complex prepared in Example 2 and the CD47 antibody (Ab) was used as a control group.

Figure 8:
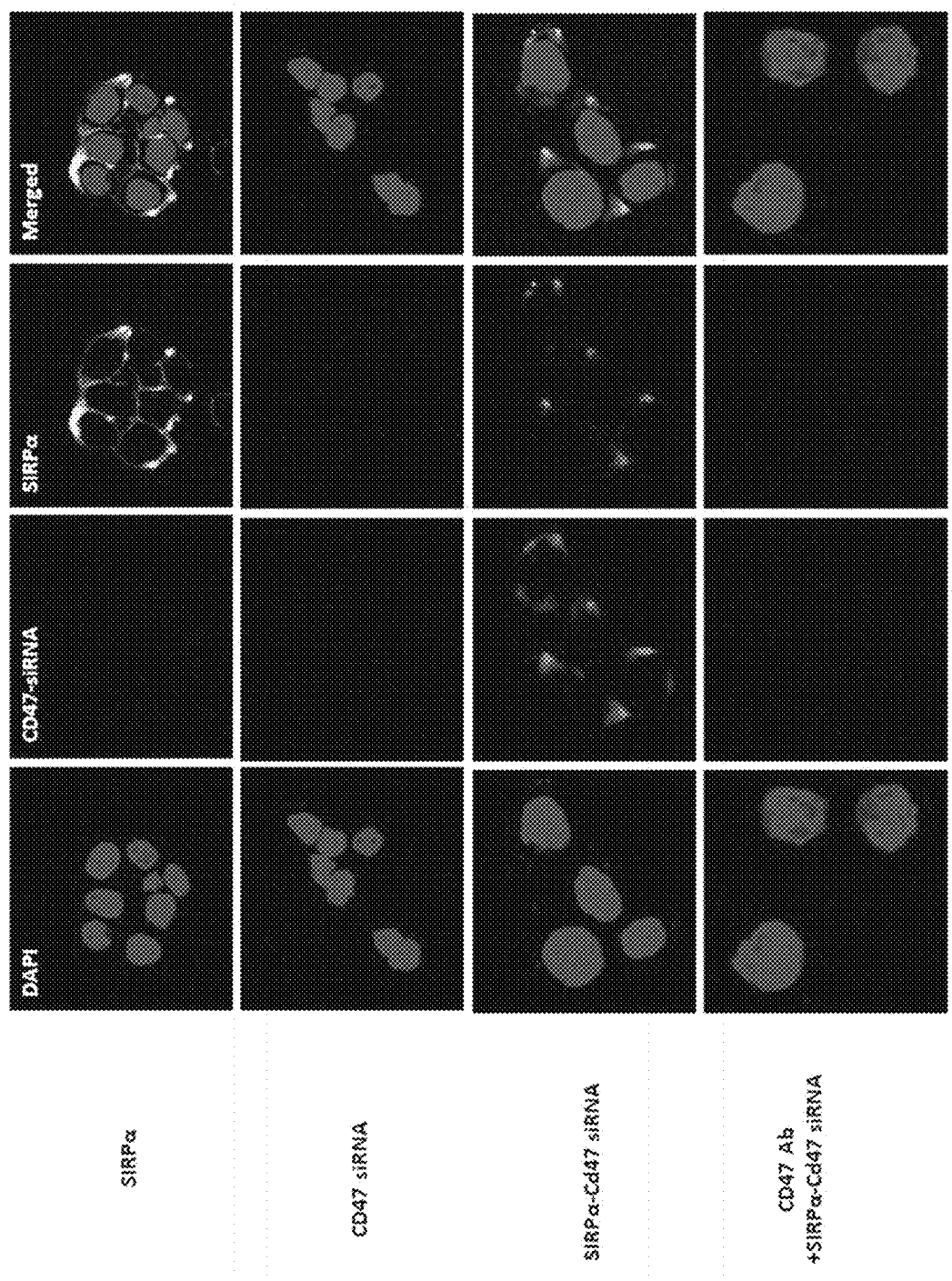
FIG. 8 shows a result of analyzing the behavior of a fusion protein-siRNA complex prepared in Example 2 in HT-29 cells by confocal microscopy.

FIG. 8 shows the confocal microscopic analysis result for identifying the behavior of the fusion protein-siRNA complex prepared in Example 2 in the HT-29 cells. In the figure, the blue color corresponds to the nuclei of the cells, the red color to the CD47 siRNA, and the green color to the SIRPα protein.

As seen from FIG. 8, it was confirmed that the fusion protein-siRNA complex prepared in Example 2 is effectively absorbed into cells. In contrast, when the CD47 siRNA was used alone, it was not absorbed into the cells at all.

In addition, it can be seen that the intracellular uptake was decreased significantly when the fusion protein-siRNA complex prepared in Example 2 was treated together with the CD47 antibody. Through this, it can be seen that the fusion protein-siRNA complex prepared in Example 2 enters the cells after binding to the CD47 receptors.

That is to say, it was confirmed through the in-vitro experiment that the fusion protein-siRNA complex prepared in Example 2 according to the present disclosure binds specifically to the receptors present on the surface of cancer cells and is effectively absorbed into the cancer cells, thereby binding to the CD47 receptors and inhibiting the immune escape mechanism of the cancer cells.

Test Example 5. Confirmation of Silencing Effect for HPRT and CD47 Genes

It was investigated whether the fusion protein-siRNA complex prepared in Example 2 has silencing effect for the HPRT and CD47 genes.

CT26.CL25 cells, which are rat colon cancer cells, were added to a serum-free medium and cultured for 4 hours after adding the fusion protein-siRNA complex prepared in Example 2. After removing replacing the medium with a serum-containing medium, the cells were cultured further for 2 days. The cultured cells were recovered and RNA was isolated using an RNA extraction kit (Rneasy Plus mini kit, Qiagen, Mettmann, Germany). The isolated RNA was subjected to RT-PCR using HPRT gene primers (F: GGC TAT AAG TTC TTT GCT GAC CTG C, R: GCT TGC AAC CTT AAC CAT TTT GGG, SEQ ID NO: 19) and CD47 gene primers (F: AGG AGA AAA GCC CGT GAA G, R: TGG CAA TGG TGA AAG AGG TC, SEQ ID NO: 20). cDNA was synthesized from 1 μg of the amplified PCR using the GoScript reverse transcription system. The synthesized cDNA was separated on 1% agarose gel and observed with an imaging apparatus using a gene stain detection solution.

In order to confirm the silencing effect for HPRT and CD47 genes in cell level, experiment was carried out on a non-treated PBS group, a group treated only with siRNA, a group treated with scramble RNA, a group treated with a complex of lipoprotein and siRNA (Comparative Example 1), a group treated with the fusion protein-siRNA complex prepared in Example 2 (SIRPα-CD47 siRNA) (−), and a group treated with the fusion protein-siRNA complex prepared in Example 2 (SIRPα-CD47 siRNA) and CD47 antibody (Ab) (+).

Figure 9:
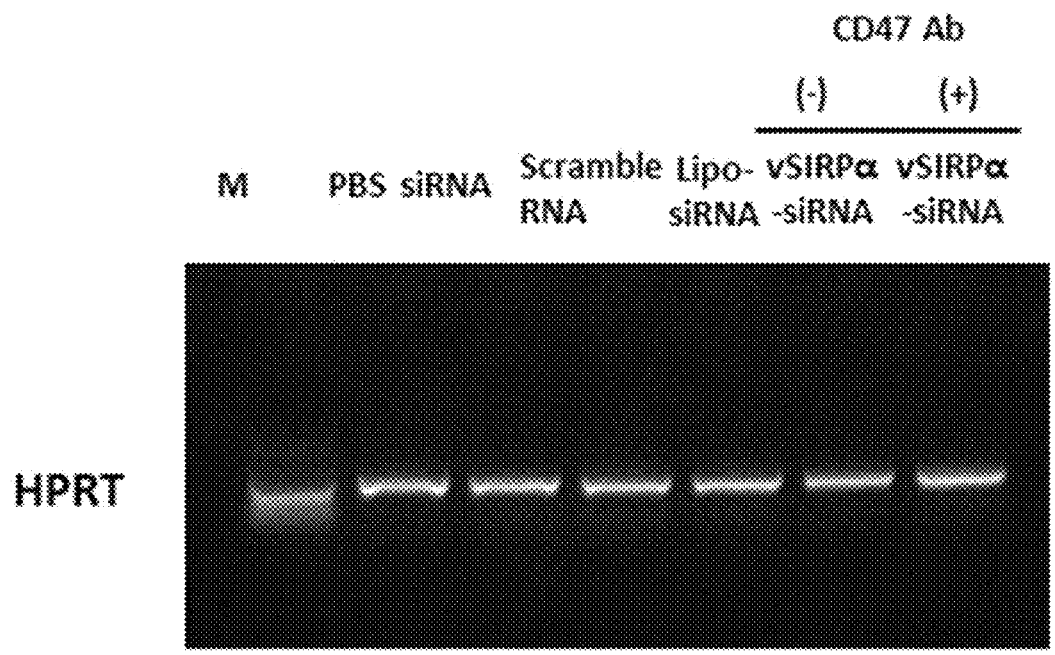
FIG. 9 shows a result of treating cancer cells (CT26.CL25) with various samples including a fusion protein-siRNA complex prepared in Example 2 (SIRPα-CD47 siRNA) and measuring the silencing effect of HPRT gene expression.

FIG. 9 shows a result of treating the cancer cells (CT26.CL25) with various samples including the fusion protein-siRNA complex prepared in Example 2 (SIRPα-CD47 siRNA) and measuring the silencing effect of HPRT gene expression. It can be seen that there is little change in the expression level of the HPRT gene.

Figure 10:
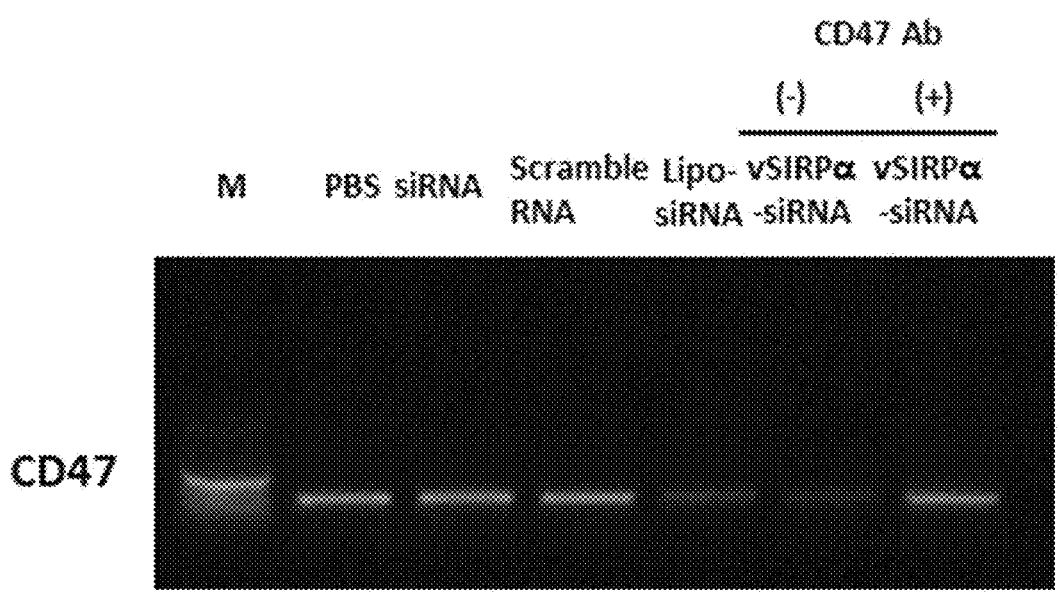
FIG. 10 shows a result of treating cancer cells (CT26.CL25) with various samples including a fusion protein-siRNA complex prepared in Example 2 (SIRPα-CD47 siRNA) and measuring the silencing effect of CD47 gene expression.

FIG. 10 shows a result of treating the cancer cells (CT26.CL25) with various samples including a fusion protein-siRNA complex prepared in Example 2 (SIRPα-CD47 siRNA) and measuring the silencing effect of CD47 gene expression. It was confirmed that the fusion protein-siRNA complex prepared in Example 2 (SIRPα-CD47 siRNA) decreases the expression of the CD47 gene to a level comparable to that of the lipofectamine-siRNA complex.

In contrast, decreased expression of the CD47 gene was not observed in the group treated together with the CD47 antibody (+) or the group treated only with siRNA.

That is to say, it was confirmed that the fusion protein-siRNA complex prepared in Example 2 (SIRPα-CD47 siRNA) is effective in decreasing the expression of the CD47 gene.

Test Example 6. Confirmation of Cytotoxicity

The cytotoxicity of the fusion protein-siRNA complex prepared in Example 2 (SIRPα-CD47 siRNA) was investigated. For this, rat colon cancer cells (CT26.CL25 cells) were treated with the fusion protein-siRNA complex prepared in Example 2 (SIRPα-CD47 siRNA) or the Lipo-CD47 siRNA complex of Comparative Example 1 at concentrations of 0, 50, 100, 200, 400 and 800 nM, and cultured for 72 hours. Then, the cells were analyzed using the CCK-8 (cell counting kit-8) kit.

Figure 11:
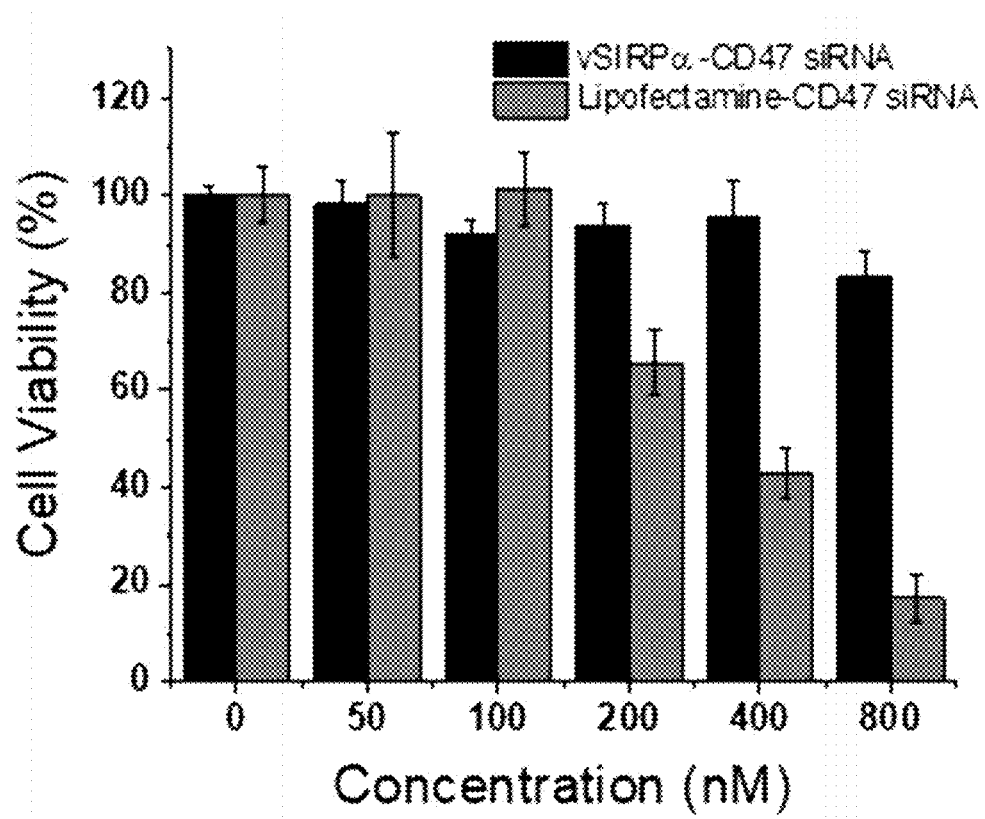
FIG. 11 shows a result of evaluating the cytotoxicity of a fusion protein-siRNA complex prepared in Example 2 (SIRPα-CD47 siRNA) and a Lipo-CD47 siRNA complex of Comparative Example 1 using CCK-8.

FIG. 11 shows a result of evaluating the cytotoxicity of the fusion protein-siRNA complex prepared in Example 2 (SIRPα-CD47 siRNA) and the Lipo-CD47 siRNA complex of Comparative Example 1 using CCK-8. It was confirmed that the cells treated with the fusion protein-siRNA complex prepared in Example 2 (SIRPα-CD47 siRNA) maintained high cell viability of 80% or higher even at high concentration (800 nM).

In contrast, the Lipo-CD47 siRNA complex of Comparative Example 1 showed toxicity at 200 nM.

Test Example 7. Confirmation of Enhanced Phagocytosis

It was investigated whether the fusion protein-siRNA complex prepared in Example 2 (SIRPα-CD47 siRNA) enhances phagocytosis by macrophages.

First, CT26.CL25 cells were treated with the fusion protein-siRNA complex prepared in Example 2 (SIRPα-CD47 siRNA) at a concentration of 200 pmol/mL and then cultured in RPMI 1640 medium (Welgene, Gyeongsan, South Korea) containing 10% FBS and 1% antibiotics (antimycotics) for two days. After the culturing was completed, the CT26.CL25 cells were stained with pHrodo Red (Invitrogen, Calif., USA) and, after adding macrophages (bone marrow-derived macrophages, BMDM) extracted from the bone marrow of a laboratory mouse (C57BL/6, male, 6-week-old), cultured for 3 hours in RPMI 1640 medium. The macrophages were stained with Green Cell Tracker (Thermo Fisher Scientific, Miss., USA) and fluorescence was measured using a fluorescence microscope (Nikon, Japan).

A control group was treated only with the SIPRα protein.

Figure 12:
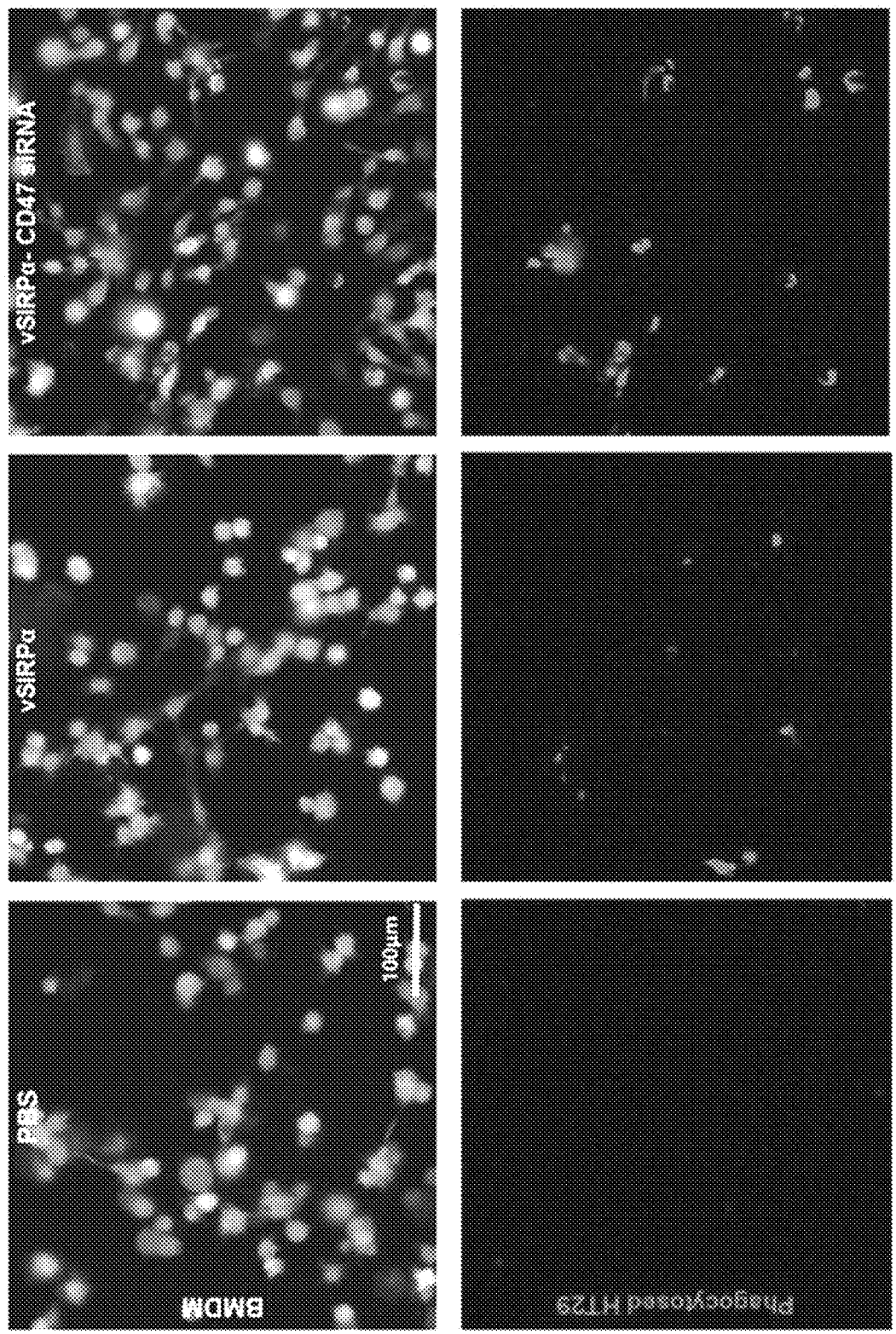
FIG. 12 shows a result of analyzing the macrophage phagocytosis effect of a fusion protein-siRNA complex prepared in Example 2 (SIRPα-CD47 siRNA).

FIG. 12 shows a result of analyzing the macrophage phagocytosis effect of the fusion protein-siRNA complex prepared in Example 2 (SIRPα-CD47 siRNA). It was confirmed that the fusion protein-siRNA complex prepared in Example 2 (SIRPα-CD47 siRNA) enhances phagocytosis by macrophages better than when the siRNA was used alone.

Under normal condition, the immunoregulatory protein SIRPα and the siRNA of the fusion protein-siRNA complex according to the present disclosure do not exhibit cytotoxicity. In the presence of tumor cells, it is taken up into the cells by reacting specifically with the receptors present on the surface of the tumor cells. It was confirmed that the fusion protein-siRNA complex absorbed into the cells is easily degraded into the immunoregulatory protein SIRPα and the siRNA by degradative enzymes present in the cells, inhibits the immunity of the cancer cells, induces silencing of the CD47 gene, and induces maximized anticancer effect by enhancing phagocytosis of the cancer cells by macrophages. In addition, it was confirmed that the intracellular delivery ability of the siRNA is enhanced and the silencing effect for the CD47 gene is also improved as compared to when only the siRNA is delivered into the cells.

The present disclosure relates to a novel double regulation-type immunoregulatory protein-target siRNA complex that is delivered specifically to tumor cells using receptors present in excessive on the tumor cells, inhibits the immune escape mechanism of the cells, and exhibits double therapeutic effect.

By using the immunoregulatory protein as a carrier for siRNA, the siRNA can be delivered specifically to cancer cell receptors and allows for doubly regulating siRNA-based anticancer immunotherapy by targeting immune-related genes.

The present disclosure provides a protein-siRNA complex wherein an immunoregulatory protein is bound to a siRNA, which is activated as it is cleaved by lysosomes after entering tumor cells. The immunoregulatory protein-siRNA complex not only improves the delivery ability to cancer cells but also maximizes anticancer therapeutic effect by doubly regulating the immune defense mechanism with the protein and the siRNA.

The immunoregulatory protein-siRNA complex is taken up by receptors overexpressed in tumor cells and exhibits medicinal effect after being degraded by lysosomes. Therefore, toxicity to normal cells can be reduced and the siRNA can function effectively in cancer cells.

What is claimed is:

1. A pharmaceutical composition comprising a fusion protein-siRNA complex consisting of an immunoregulatory fusion protein (A); and a siRNA (B);

wherein the immunoregulatory fusion protein (A) is one in which SIPRα protein is bound to a linker peptide cleavable by a lysosomal degradative enzyme, and the siRNA is CD47 siRNA, wherein the SIPRα protein comprises an amino acid sequence of any one of SEQ ID NOs: 3, 5, 7, 9 and 11, and the linker peptide comprises an amino acid sequence of SEQ ID NO: 13.

2. A pharmaceutical composition comprising a fusion protein-siRNA complex consisting of an immunoregulatory fusion protein (A); and a siRNA (B);

wherein the immunoregulatory fusion protein (A) is one in which SIPRα protein is bound to a linker peptide cleavable by a lysosomal degradative enzyme, and the siRNA is CD47 siRNA, wherein the immunoregulatory fusion protein (A) comprises an amino acid sequence of SEQ ID NO: 1.

3. The pharmaceutical composition according to claim 1, wherein the siRNA comprises an amino acid sequence of SEQ ID NO: 17 or 18.

4. The pharmaceutical composition according to claim 1, wherein the fusion protein-siRNA complex has an average molecular weight of 20-60 kDa.

5. The pharmaceutical composition according to claim 2, wherein the siRNA comprises an amino acid sequence of SEQ ID NO: 17 or 18.

6. The pharmaceutical composition according to claim 2, wherein the fusion protein-siRNA complex has an average molecular weight of 20-60 kDa.

* * * * *